(12) United States Patent
Cereceda Balic et al.

(10) Patent No.: US 9,791,151 B2
(45) Date of Patent: Oct. 17, 2017

(54) CONTROLLED COMBUSTION SYSTEM

(76) Inventors: Francisco Javier Cereceda Balic, Quilpue (CL); Mario Gonzalo Toledo Torres, Vina del Mar (CL)

( * ) Notice: Subject to any disclaimer, the term of this patent is extended or adjusted under 35 U.S.C. 154(b) by 1143 days.

(21) Appl. No.: 13/977,825

(22) PCT Filed: Dec. 30, 2010

(86) PCT No.: PCT/CL2010/000058
§ 371 (c)(1),
(2), (4) Date: Jul. 1, 2013

(87) PCT Pub. No.: WO2012/088617
PCT Pub. Date: Jul. 5, 2012

(65) Prior Publication Data
US 2013/0280663 A1 Oct. 24, 2013

(51) Int. Cl.
*F23N 5/00* (2006.01)
*G01N 25/26* (2006.01)
*G01N 25/00* (2006.01)
*G01N 33/00* (2006.01)

(52) U.S. Cl.
CPC ............. *F23N 5/003* (2013.01); *G01N 25/26* (2013.01); *F23N 5/00* (2013.01); *F23N 2900/00* (2013.01); *G01N 25/00* (2013.01); *G01N 33/004* (2013.01); *G01N 33/0037* (2013.01); *G01N 33/0042* (2013.01)

(58) Field of Classification Search
CPC ........ F23N 5/003; F23N 5/00; F23N 2037/00; F23N 2900/00; G01N 25/26; G01N 25/00
USPC ....................................................... 431/13, 2
See application file for complete search history.

(56) References Cited

U.S. PATENT DOCUMENTS 2,821,067 A    1/1958   Hill
4,054,414 A *  10/1977  Grob ...................... G01N 30/66
                                                       422/89

(Continued)

FOREIGN PATENT DOCUMENTS

JP    2006125726 A    5/2006
JP    2006150705 A    6/2006
JP    2006266546 A    10/2006

OTHER PUBLICATIONS

Salvador et al., "Combustion of a substitution fuel made of cardboard and polyethylene: influence of the mix characteristics experimental approach", Fuel, 2004, p. 83.

(Continued)

*Primary Examiner* — Dennis M White
*Assistant Examiner* — Bryan Kilpatrick
(74) *Attorney, Agent, or Firm* — Law Office of Jeff Williams; J. Oliver Williams

(57) ABSTRACT

The invention relates to a controlled combustion system for the simultaneous analysis of the thermodynamic efficiency of combustion and total polluting emissions in solids with combustible potential, including: a pre-chamber, a combustion chamber, a heat transfer unit which includes a connection for a device that analyses combustion gases to determine the performance of combustion and burning, and a unit for storing the combustion emissions, which comprises a container for storing the sample and a means of collecting samples for the simultaneous collection of gases and particulate matter for analyzing the combustion emissions.

23 Claims, 8 Drawing Sheets

(56) References Cited

U.S. PATENT DOCUMENTS

| | | | | |
|---|---|---|---|---|
| 4,087,249 A | * | 5/1978 | Okumoto | G01N 31/12 422/78 |
| 4,270,930 A | | 6/1981 | Cambell | |
| 2002/0080849 A1 | * | 6/2002 | Lyon | G01N 31/12 374/36 |

OTHER PUBLICATIONS

Aracil et al., "Semivolatile and volatile compounds from the pyrolysis and combustion of polyvinyl chloride", J. Anal. Appl. Pyrolysis, 2005, p. 74.

Kannan et al., "Estimation of gaseous products and particulate matter emission from garden biomass combustion in a simulation fire test chamber", Atmospheric Environment, 2005, p. 39.

Ferge et al., "On-Line Analysis of Gas-Phase Composition in the Combustion Chamber and Particle Emission Characteristics during Combustion of Wood and Waste in a Small Batch Reactor", Environmental Science & Technology, 2005, p. 39.

* cited by examiner

CONTROLLED COMBUSTION SYSTEM

TECHNICAL FIELD

The present invention relates to a controlled combustion system for the simultaneous analysis of combustion thermodynamic efficiency and analysis of total polluting emissions (gases and particulates) in solids with combustible potential and a operative method of the controlled combustion system.

BACKGROUND

The present invention is related to patent application CL200800843 on 24 Mar. 2008, of the same applicant, which is cited as a reference herein. It provides an improved and corrected version of the invention already mentioned.

The development of controlled combustion chambers is not new, one of the first registered patents is the U.S. Pat. No. 2,821,067, on 28 Jan. 1958, entitled "Combustion chamber construction in a gas turbine engine", by Hill, Henry C., whose primary objective was focused on defining the layout of the first internal combustion engines. These combustion chambers were designed to work based on fossil fuels.

Currently, the new environmental regulations and decreased global reserves of fossil fuels, are massifying the use of the so called "alternative fuels". In this new scenario, it has been observed that the combustion chambers were developed in two main areas.

The first of these areas is related to equipment which might be used both for industrial and domestic energy production, associated with the use of alternative solid combustibles like biomass, such as wood, waste from agriculture and forestry industry, industrial and domestic solid residues, among others. Examples of these developments are the U.S. Pat. No. 4,270,930, dated on 2 Jun. 1981, and entitled "Clean combustion chamber fuel composition", by Cambell Curtis B. and Peyla Richard J.; and the applications JP2006125726, dated on 18 May 2006, titled "Combustion chamber with window for wood pellet stove", by Matsumoto Hiromasa, JP2006266546, dated on 5 Oct. 2006, titled "Wood pellet fuel combustion system", by Tsuneo Kaneko and Omi Shuji, and JP2006150705, dated on 15 Jun. 2006, titled "Smoking/Drying apparatus and wood smoking/drying method", by Muneda Yuji.

These documents describe mainly furnace and chimney in whose development has been worked in some cases to increase the thermodynamic efficiency of combustion and in other cases to minimize the emission of particulate matter. These generic combustion chambers have low operational flexibility as they have been developed to meet specific goals as provide energy for heating or cooking, and for the most part the design only allows the use of one type of fuel. None of these chambers have been designed with the purpose of being used as a laboratory chamber for research and independent or simultaneous analysis of both emissions from combustion, solid contaminants such as particulate matter (PM) and gaseous, to measure the thermodynamic efficiency of a given process of combustion.

The second area of development is in the research. In this field, we find scientific articles published in specialized journals in which it is reported a large number of controlled combustion chambers ("Combustion of a substitution fuel made of cardboard and polyethylene: influence of the mix characteristics experimental approach", Fuel 83 (2004), Salvador et.al, "Semivolatile and volatile compounds from the pyrolysis and combustion of polyvinyl chloride", J. Anal. Appl. Pyrolysis 74 (2005), Aracil et.al, "Estimation of gaseous products and particulate matter emission from garden biomass combustion in a simulation fire test chamber", Atmospheric Environment 39 (2005), Kannan et.al, "On-Line Analysis of Gas-Phase Composition in the Combustion Chamber and Particle Emission Characteristics during Combustion of Wood and Waste in a Small Batch Reactor", Environmental Science & Technology 39 (2005), Ferge et.al), though each one of them has been developed for specific purposes that each research group had raised, whereby, similar to the case of the development of equipment for domestic and industrial use, these combustion chambers have low operational flexibility and none of them is oriented to the research and simultaneous analysis of thermodynamic efficiency and emissions of a determined combustion process.

BRIEF DESCRIPTION OF THE INVENTION

The present invention provides a controlled combustion system that allows the simultaneous measurement of combustion efficiency and burning of solid materials and the analysis of the total emission of pollutants, both solid and gaseous by generating different combustion processes through the flow control of oxidizer (air or oxygen) and/or mass of fuel.

The system can be used in all research areas related to solid alternative fuels, from feasibility studies of the use of solid as fuel, performance and energy efficiency to equipment design and/or operation, that this type of fuel uses.

Another application of the invention is in the area of pollutant emissions which can be used in the complete identification of emission profiles, emissions factors for each type of contaminants, molecular markers and concentration ratios of specific chemical compounds by type pollution sources as well as obtain chemical and/or physical characterization of the emitted compounds, since as being able to collect all the gases and particulate matter generated during combustion, it is possible to perform a mass and energy balance for different types of solid combustible, providing versatility regarding the amount and types of analysis that can be performed on the collected samples.

Is important to emphasize, that most of the combustion chambers as indicated in the prior art search opt to use dilution devices of emissions that generate the studied combustion processes mainly due to the huge amount of samples (particles and gases) that are produced in these processes, which must be diluted in order to use sampling and analysis systems available on the market today; these devices are generally referred as dilution tunnels (DT). Unfortunately, these DT obviously do not allow taking the whole sample and the dilution or separation process of a portion of the sample for its collection and/or analysis may undergo artifact of sampling, which results in a modification of the physicochemical characteristics of the original sample, producing erroneous results and inducing therefore to misinterpretation of results. Unlike the described systems, the present invention is designed to take all of gaseous and particulate emissions produced by the combustion process, so that the sample and its subsequent analysis are as representative of the process to be characterized as possible by minimizing as far as possible the problems of sampling artifact, a feature that no other system can offer.

Another fundamental contribution of this invention lies in the capacity to perform simultaneous analysis in both application areas, which to date no other system can do. This capability is a benefit for the user from the perspective of which reduces the number of experience required to characterize the solids combustion with energy potential, because from the same experience the information necessary is gained to perform both burning and combustion performance analysis, and pollutant emissions analysis, where combustion performance is the energy loss associated with the excess of air used in the combustion process and the burning performance considers the achieved amount of fuel being fully burned and evaluates the unburned fuel losses that appears in the combustion process emissions. This will reduce logistics costs of research and characterization of a given combustion process.

Furthermore, the invention enables the user to define the values for high impact variables about the combustion process and emissions at will, such as setting a quantity of solid to be used for each batch of combustion and controlling the flow of oxidizer (air and/or oxygen), i.e. defining an air-fuel ratio, so during the combustion process you can measure the temperature of the combustion zone, and emissions and temperature of gases.

The main benefit of this type of simultaneous analysis is that allows to associate an environmental variable with an operational variable, becoming itself not only into a tool for analyzing pollutant emissions, but in a system of generation of varied scenarios of combustion, which allows to determine, for instance, operating conditions to deliver maximum combustion efficiency with minimal emission of pollutants.

The controlled combustion system also reduces work hours invested in general because, on the one hand, data for two analyses from a single experience are obtained and, on the other hand, automating the operation of the system allows the operator to perform other activities while combustion takes place. Additionally, the control and automation of the operation system allows repeatable and reproducible experiences, dramatically improving the quality control and quality assurance of the results obtained with the invention.

The main objectives for the controlled combustion system are:

Obtaining reproducible and repeatable combustion conditions;

Collecting all the gases and particulate matter generated during the combustion process;

Obtaining data to determine emission factors for each type of pollutant, molecular markers and concentration ratios of specific chemicals compounds per type of pollution sources, as well as obtaining the chemical and/or physical characterization of the emitted compounds;

Obtaining data to determine the combustion and burning efficiency;

Allowing the variability of different combustion parameters in order to optimize simultaneously the maximum combustion and burning efficiency, and the minimum emissions.

The sample collected from the combustion process has multiple analysis options, including analysis of organic and inorganic compounds which allows to determine specific emissions profiles for the analyzed solids; size analysis, morphology and number of emission particulates, among others. Moreover, the data of concentration of CO, $CO_2$, and oxygen, among others, allows determining the combustion and burning efficiency. In this way is possible to obtain simultaneous analysis of both pollutant emissions and combustion and burning efficiency by each experience.

A first objective of the invention is to provide a controlled combustion system for the simultaneous analysis of pollutant emissions and combustion thermodynamic efficiency in solids with combustible potential, comprising a prechamber or unit, preferably cylindrical, which is formed with guides for the positioning of a solid combustible through an ashtray, a peephole, an oxidizing gas injection pipeline and a first glass ring to isolate the high temperature of the combustion zone; a unit or combustion chamber, preferably cylindrical, connected to the prechamber, which contains an adiabatic furnace for the combustion of solid combustible, ignited by an electrical resistance, located on the ashtray, for each batch of combustion; a heat transfer unit, preferably cylindrical, connected downstream of the combustion chamber, comprising a connection for a combustion gases analyzer device to determine the combustion and burning efficiency, a second glass ring to isolate the high temperature of the combustion zone, and a storage unit of combustion emissions, connected downstream of the heat transfer section with binding and fastening medium containing a sample storage container and means for sampling for the simultaneous collection of gases and particulate matter obtained in the combustion chamber, in order to perform analyzes of combustion emissions with such collection. Furthermore, the system is constructed of chemically inert material resistant to combustion temperatures. The prechamber allows the injection of oxidizer and positioning of the solid combustible in the ashtray inside the combustion chamber. In the ashtray, which is connected to the oxidizer injection pipe, the solid combustible is placed, where also is installed an electrical resistance for the ignition of the solid combustible and a sensor that measures the temperature in the combustion zone. Where the positioning of the solid combustible inside the combustion chamber is achieved by depositing the solid combustible in the ashtray, which is guided through the prechamber manually into the said combustion chamber through four equally spaced concentric guides which are subjected to a conical cover which in turn hermetically seals the combustion chamber before the combustion process begins. Moreover, the prechamber has a cold zone cylindrical first structure, a second cold zone cylindrical structure, a hot zone cylindrical structure and a glass front cover attached to the prechamber for visual analysis of the combustion zone.

The adiabatic furnace is constructed with refractory ceramic and equipped with an electrical resistance that generates the temperature necessary to maintain the combustion chamber adiabatically during the process of combustion and is, at the same time, surrounded by a heat insulating to prevent heat losses to the environment. The heat transfer unit, the length of the cylindrical tube is calculated using a heat transfer model especially designed for the combustion chamber to achieve a suitable temperature for combustion emissions and then be received and analyzed in the area for storing combustion emissions. At the start of the heat transfer unit is installed a gas analyzer, which can measure, among other chemicals, CO, $CO_2$, $NO_x$, $SO_x$, $O_2$ and temperature, where the measured $CO_2$ allows to determine the combustion and burning efficiency. In the heat transfer unit and prior to the combustion emission storage unit, a secondary air injection nozzle is located, which serves to cool down the combustion emissions and increase the flow rate of the emissions as required for the storage unit of combustion emissions. The storage unit container of combustion gases and particles emissions is made of a flexible material, chemically inert. Also serves as a storage lung of the emissions, gases and particles, from where samples are taken through four or more connections for sampling where different devices are connected for taking samples and subsequent analysis. The operational control of the controlled combustion system is conducted through a control electronic device which delivers automatic a versatility of options with high reproducibility and repeatability between each experiment carried out at the same conditions. Finally, for the operation, the controlled combustion system is supported by three clamps supports; and for the cleaning of the controlled combustion system "clamp" joints ensure an easy assembly and dismantling of the units of the controlled combustion system.

Another objective of the invention is to provide an operative method for the controlled combustion system for the simultaneous analysis of combustion thermodynamic efficiency and polluting emissions analysis in solids with energy potential which comprises injecting an oxidizing gas to a combustion system controlled through oxidizing gas injection at one end of a unit or prechamber, preferably cylindrical, where said pre-chamber is conformed with guides for the positioning of a solid combustible through an ashtray, one peephole, a oxidizing gas injection pipeline, and a first glass ring to isolate the high temperature of the combustion zone; define a variable central volume that creates a flame zone in a unit or combustion chamber, preferably cylindrical, connected to the other side of the prechamber, for an amount of solid combustible to be used for each batch of combustion; recording parameters of combustion temperature in a heat transfer unit, preferably cylindrical, connected downstream of the combustion chamber, comprising a connection for a combustion gases analyzer device to determine the combustion and burning performance, a second ring of glass to isolate the high temperature of the combustion zone; simultaneously collect and store gases and particulate matter obtained from combustion, with a storage unit of combustion emissions, connected downstream of the heat transfer unit; analyze pollutant emissions of organic and inorganic compounds for determining emission profiles, emission factors for each type of pollutant, molecular markers and concentration ratios of specific chemical compounds per pollutant source type, for solids analyzed; and obtain simultaneous results of thermodynamic efficiency and pollutant emissions analysis in combustion solids. To inject the oxidizing gas, the prechamber is conformed to guides for the positioning of an ashtray, one peephole, an oxidizing gas injection pipeline, and a first glass ring to isolate the high temperature of the combustion zone. The combustion chamber contains an adiabatic furnace for the combustion of the solid combustible. In addition, the gas analyzer can measure, among other chemical compounds, CO, $CO_2$, $NO_x$, $SO_x$, $O_2$ and temperature, where the measured $CO_2$ allows determining the combustion and burning efficiency. The temperature in the combustion zone is measured by a sensor. The positioning of the solid combustible into the combustion chamber is achieved in the prechamber, by guiding an ashtray into the said combustion chamber manually through four equally spaced concentric guides that are subject to a conical cover, which hermetically seals the combustion chamber before the combustion process starts. Moreover, the prechamber has a first cold area cylindrical structure, a second cold area cylindrical structure, a hot area cylindrical structure and a glass front cover attached to the prechamber for a visual analysis of the combustion zone. In the heat transfer unit and prior to storage combustion emissions unit a secondary air injection nozzle is located, to cool down the combustion emissions and to increase the flow rate of emissions as required for the combustion emissions storage unit. Furthermore, the storage unit of combustion emissions comprises a container, of inert material, that serves as a emission storage lung where samples are collected through four or more connections for taking samples where different sampling devices are connected for the collection of samples and subsequent analysis. The operational control of the controlled combustion system is conducted through an automatic electronic device which delivers versatility of options with high reproducibility and repeatability between each experiment carried out at the same conditions.

DESCRIPTION OF A PREFERRED EMBODIMENT

Figure 1:
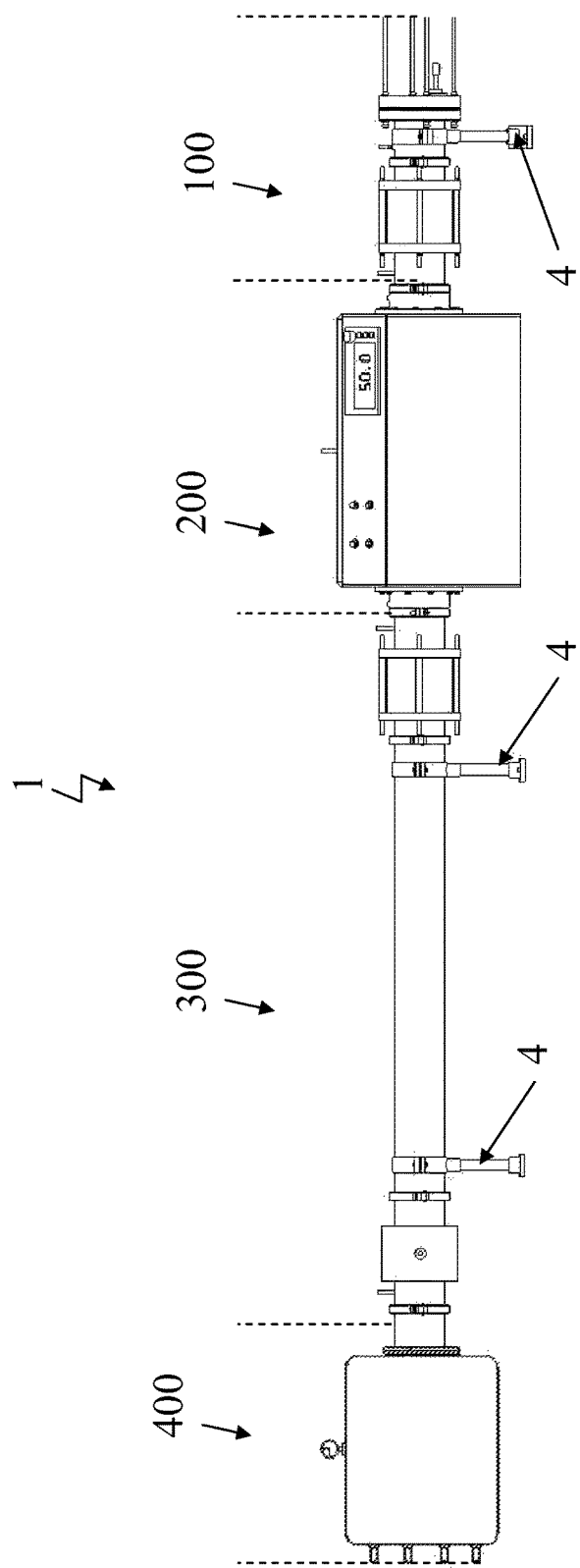
FIG. 1 shows a general view of the controlled combustion system of the present invention.
Figure 2:
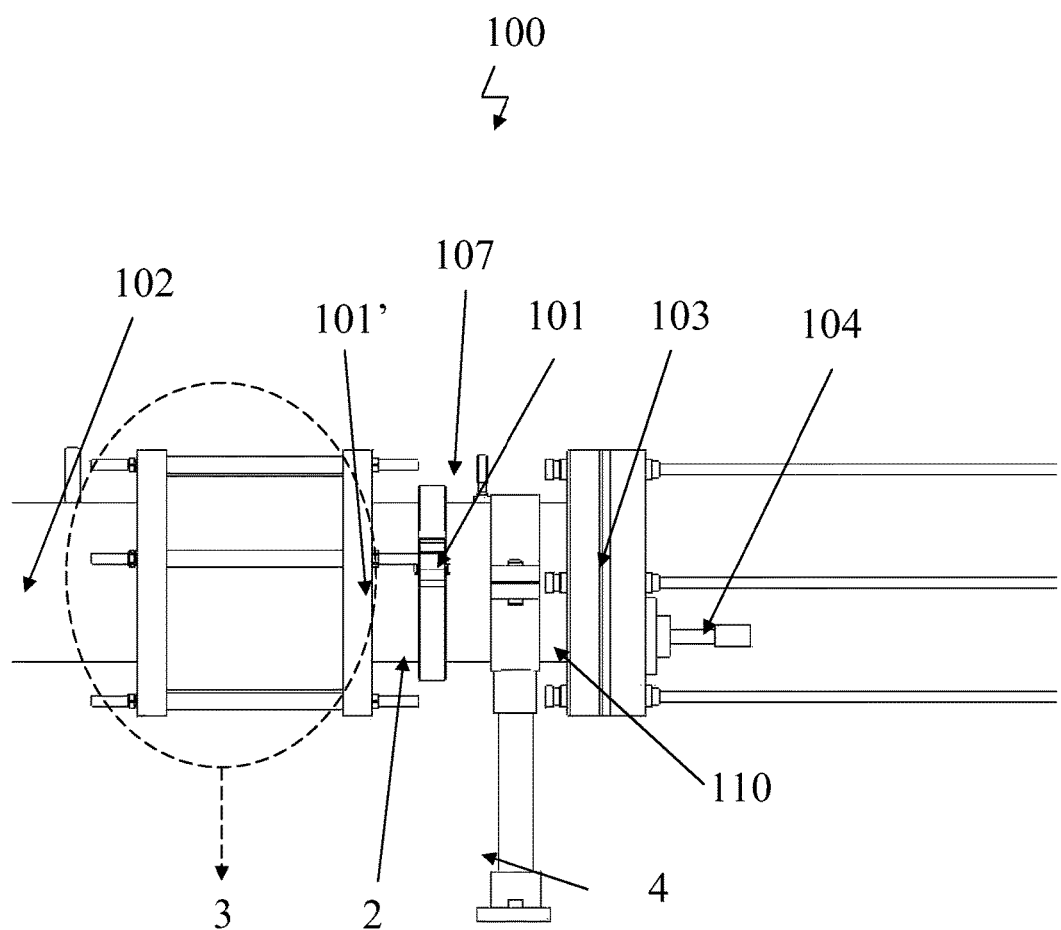
FIG. 2 shows a view of the pre-chamber of the controlled combustion system of the present invention.
Figure 3:
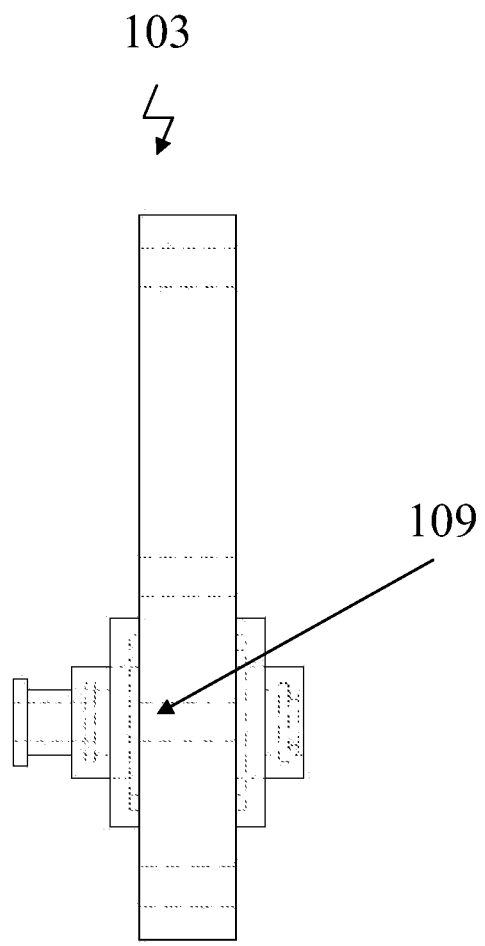
FIG. 3 shows a view of the peephole of the prechamber of combustion.
Figure 4:
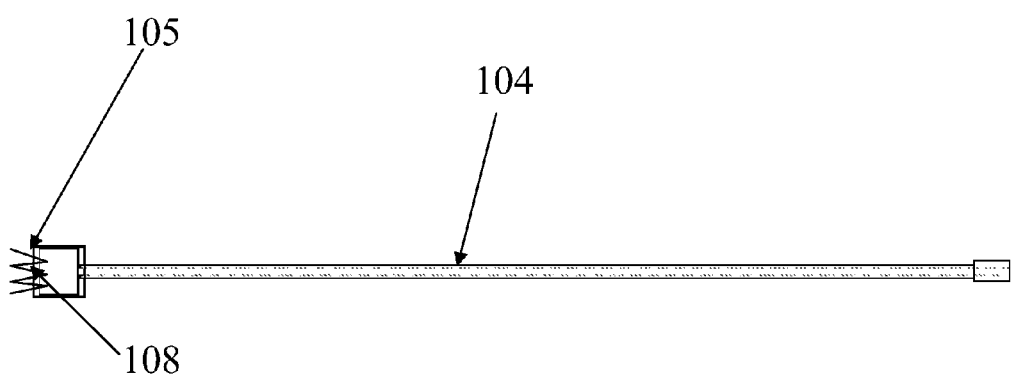
FIG. 4 shows the ashtray with the oxidizing injection pipeline.

The controlled combustion system (1), in its functional aspect comprises four units made of stainless steel, preferably 316 stainless steel, with both high mechanical and thermal resistance. The first unit is a prechamber (100) that allows the injection of oxidizer and the positioning of the solid combustible into a second unit which corresponds to the combustion chamber (200); the third unit is called the heat transfer area (300) consists of a device which ensures the connection between the combustion chamber at high temperature, with a fourth unit called combustion emissions storage area (400).

The prechamber (100) contains a piece formed by an ashtray (105) and an oxidizing injection pipeline (104), and is capable of withstand very high temperatures, in order to contain materials that are desired to burn. The solid combustible is positioned in the ashtray (105), where are additionally installed an electric resistance (108) to ignite the solid combustible and a sensor that measures the temperature in the combustion zone. The oxidizing is injected through the oxidizing injection pipeline (104), so as to directly feed the fuel. The positioning of the solid combustible into the combustion chamber (200) is achieved through the prechamber (100) which allows to manually guide the ashtray (105) into the said combustion chamber (200) through four concentric equidistant guides that are subject to a conical cover (110) which in turn hermetically seals the combustion chamber (200) before the start of the combustion process. Moreover, the same conical cover (110) of the prechamber (100) contains a glass front cover (103) for visual analysis of the combustion zone, and an insulating element for quick and easy coupling, consisting of a first glass ring (3) minimizing the conductive heat transfer between the prechamber (100) and the combustion chamber (200).

The combustion chamber (200) takes the mass of solid combustible through the ashtray (105) where the solid combustible ignition is performed. The combustion chamber (200) is formed by a cylindrical tube which is inserted in an adiabatic furnace (203) constructed with refractory ceramic and equipped with an electrical resistance that generates the temperature necessary to maintain the combustion chamber (200) as adiabatic throughout the combustion process, the furnace is in turn wrapped by a heat insulator to prevent heat losses to the environment, not shown in the figure.

The heat transfer area (300) consists of a stainless steel cylinder (303) of the same diameter of the combustion chamber (200) which has a second glass ring (3) that minimizes the conductive heat transfer between the combustion chamber (200), at high temperature, and the storage area of combustion emissions (400) which requires a temperature equal to or below 85° C. for operation.

Additionally, the length of the cylindrical tube of the heat transfer area (300) is calculated using a heat transfer model especially designed for this combustion chamber (200) to achieve a suitable temperature for combustion emissions and then be received and analyzed in the storage area of combustion emissions (400). At the beginning of the heat transfer area (300) the gas analyzer is installed, which can measure, among other chemicals, CO, $CO_2$, $NO_x$, $SO_x$, $O_2$ and temperature, where the $CO_2$ measured allows to determine combustion and burning performance. Furthermore, the heat transfer area (300) and prior to the storage area for combustion emissions (400), a secondary air injection nozzle (306) is located, which serves to cool combustion emissions and to increase the flow rate as required for the storage area of combustion emissions (400). The combustion emissions storage area (400) preferably comprises a flexible container (401), of a chemically inert material, such as Tedlar® or Teflon®, and four or more connections for taking samples (402) and suitable, for example, for sampling through sampling devices (cartridges), as used in the equipment called Speciation Sampler®, 2300® Partisol Thermo® signature, USA. In each of the sampling devices can be collected samples for different tests, such as analysis of semivolatile organic compounds (COSVs) in particulate matter, or in gas phase, analysis of volatile organic compounds (VOCs), gravimetry of particulate matter from different aerodynamic diameters ($PM_{2.5}$; $PM_{10}$, etc.), particle size distribution, among other possible analyzes. The main objective of the combustion emissions storage area (400) is to collect the gases and particulate matter generated in the combustion chamber (200) for chemical/or physical emissions characterization. The flexible container (401) serves as emissions storage lung, where samples are taken through four or more connections for taking samples (402) in which different devices are connected to sampling and subsequent analysis.

In order to achieve each of the main objectives, the design of the controlled combustion system (1) has the following features:

Oxidizing flow control, mass amount and type of solid combustible: These variables generate significant differences within the combustion process if they are modified, directly affecting emissions and combustion and burning performance. Furthermore, the operational control of the controlled combustion system is performed through an automatic control electronic device which delivers versatility options with high reproducibility and repeatability between each experiment carried out at the same conditions.

Oxidizing direct injection to the solid combustible: The oxidizing injection pipeline (104) gives the oxidizing to the solid combustible directly that is on the ashtray directly. This ensures that the oxidizing in full contact with the solid combustible, and thus not cause errors in the air-fuel ratio (RAC) which you want to work with.

Elimination of memory effect: The construction material of the controlled combustion system (1) provides a wide range of possibilities for cleaning after each experience, ranging from total pyrolysis to mechanical and/or chemical abrasion. Moreover, the controlled combustion system (1) has the characteristic of being very easily assembled and disassembled due to quick type "clamp" joints (2) that binds each of the different units. Thus, it is ensured that from an experience and the next there are no disturbances in memory effect in the controlled combustion system (1).

Analysis of combustion gases: controlled combustion system (1) has a combustion gas analyzer (not shown) that works continuously, located at the exit of the combustion chamber (200) or on the entrance of the heat transfer area (300), which delivers the required data to perform studies of combustion and burning efficiency of each test. Additionally, emission samples allow to obtain emission factors for each type of pollutant, molecular markers and concentration ratios of specific chemical compounds by type of pollution sources and to obtain chemical and/or physical characterization of the emitted compounds.

The invention in its constructive aspect, shown in FIG. 1, consists of a controlled combustion system (1) comprising a prechamber (100), a combustion chamber (200), one heat transfer zone (300), and a combustion emissions storage area (400).

As shown in FIGS. 2 to 5, the pre-chamber (100) is mainly designed in a first cold zone cylindrical structure (101) and a second cold zone cylindrical structure (101') and a hot zone cylindrical structure (102), a glass front cover (103), a first glass ring (3) to minimize heat transfer by conduction, and an ashtray (105), connected with a oxidizing injection pipeline (104).

The glass front cover (103) has a perforation (109) at its bottom, which serves to guide the oxidizing injection pipeline (104), to scroll the ashtray manually through the prechamber (100) and combustion chamber (200) through four equally spaced concentric guides. In the ashtray (105) an electrical resistance (108) is located, which serves to ignite the solid combustible and a K-type thermocouple for sensing the temperature of the combustion zone.

Figure 5:
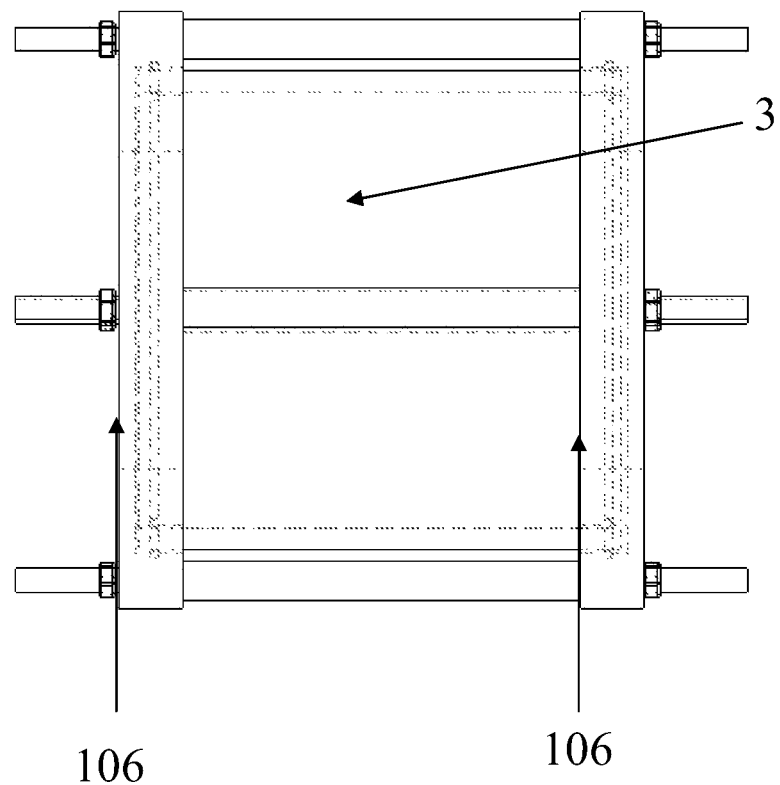
FIG. 5 shows a view of the glass ring and its fastening system to the prechamber and to the heat transfer unit.
Figure 6:
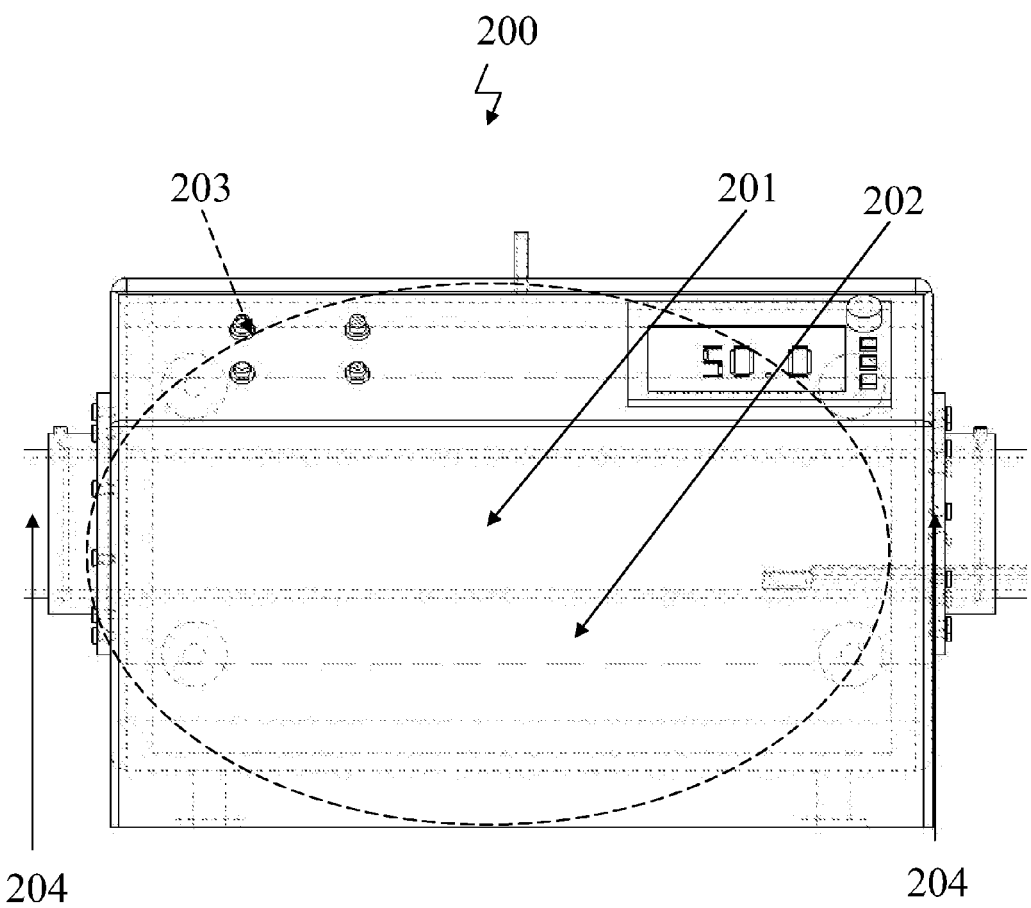
FIG. 6 shows a view of the combustion chamber of the controlled combustion system of the present invention.
Figure 7:
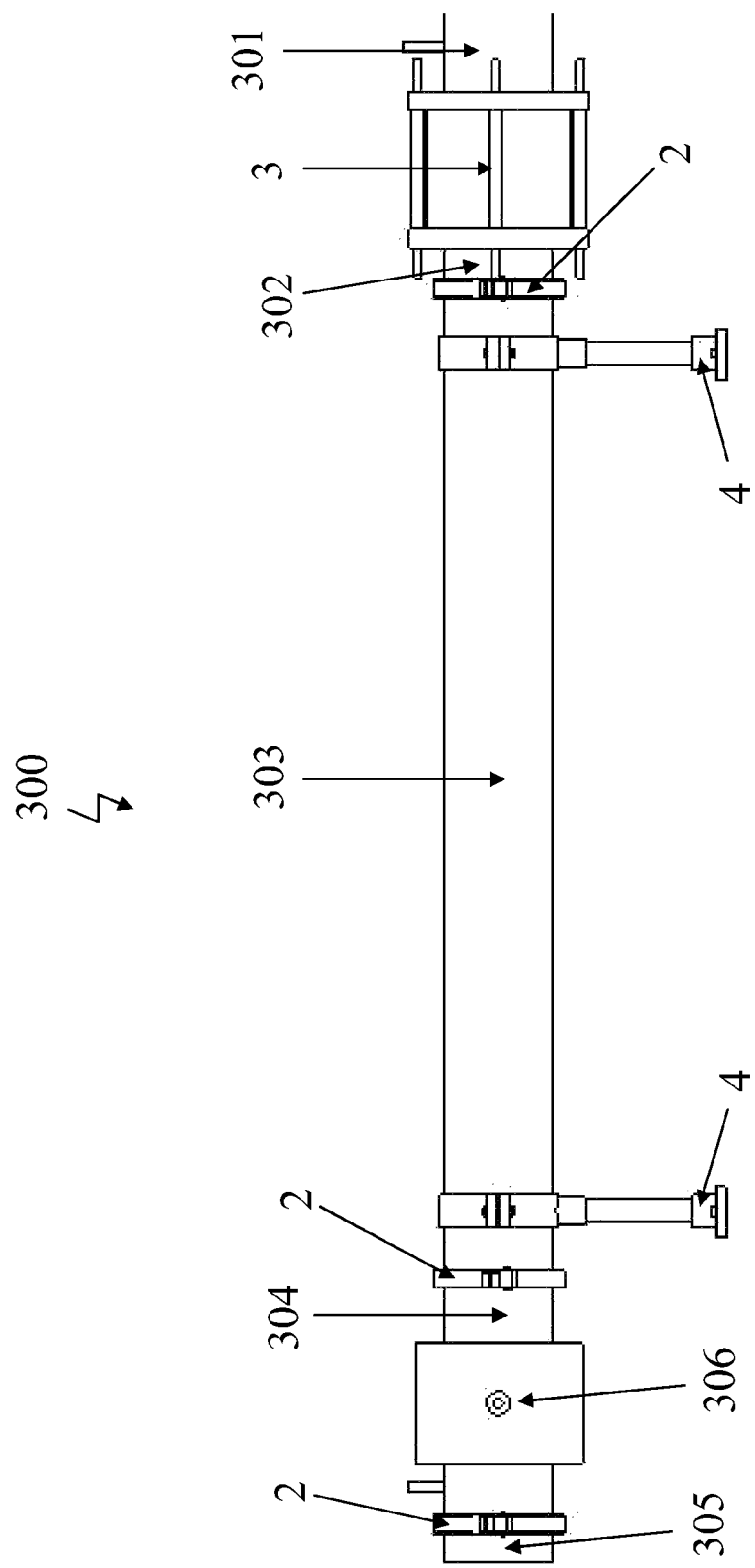
FIG. 7 shows a view of the heat transfer unit
Figure 8:
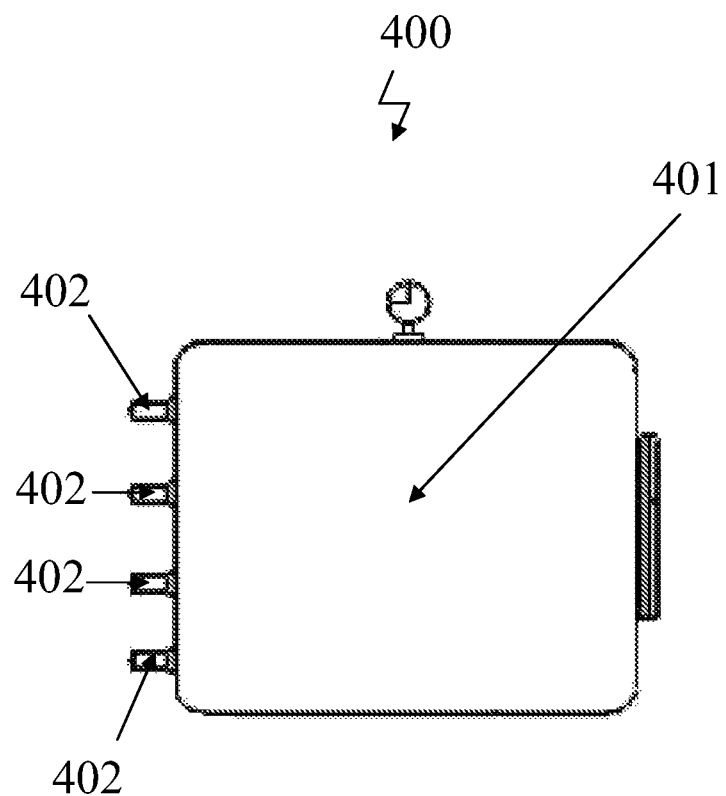
FIG. 8 shows a view of the combustion emissions storage unit of the controlled combustion system of the present invention.

The glass front cover (103) is connected through four bolts to a conical cap (110), where the latter is joined to the first cold zone cylindrical structure (101), which in turn binds to the second cool zone cylindrical structure (101') through a type "clamp" joint (2). Then, the second cold zone cylindrical structure (101') connects the first glass ring (3) to minimize heat transfer by conduction from the combustion chamber (200), the first glass ring (3) contains two connecting rings (106) which are joined through four bolts as shown in FIG. 5. Then, the first glass ring (3) is connected to the hot zone cylindrical structure (102), which in turn binds to the combustion chamber (200), through a type "clamp" joint (2). In the cold zone cylindrical structure (101) a pressure gauge (107) is mounted, which measures the pressure of the controlled combustion system (1) as a whole.

The type "clamp" joints (2) ensure easy assembly and disassembly of the controlled combustion system (1).

The combustion chamber (200) is constituted by an adiabatic furnace (203) consisting of a cylindrical pipe (201) of the same diameter as the pre-chamber (100), an electrical resistance, a thermal insulator (202) and two seals (204) of the combustion chamber (200) in each end. These seals (204) are attached, on one side, to the pre-chamber (100) through a type "clamp" joint (2) and, on the other side, to the heat transfer area (300), through a type "clamp" joint (2) too.

The heat transfer area (300), comprises mainly a section of a hot zone cylindrical pipe (301) and four sections of cold zones cylindrical pipe (302, 303, 304, 305) of equal diameter to the combustion chamber (200), a second glass ring (3) to minimize heat transfer by conduction, which is equal to the one in the pre-chamber (100), and an secondary air injection nozzle (306). This secondary air injection nozzle (306) serves to cool the combustion emissions and to increase the flow rate of the emissions to ensure the proper functioning of the connections for sampling.

In the section of hot zone cylindrical pipe (301) the gas analyzer which measures, for instance, CO, $CO_2$, $NO_x$, $SO_x$, $O_2$ and the gas temperature, among others, is installed so as to calculate the performances of combustion and burning. One end of the section of hot zone cylindrical pipe (301) is connected to the combustion chamber (200) through a joint of "clamp" type (2), and the other end is connected to the second glass ring (3) to minimize heat transfer by conduction, which in turn is connected to the first pipe of cold zone (302). Then, the first section of cold zone cylindrical pipe (302) joins the second pipe of cold zone (303) through a clamp joint (2). The second section of cold zone cylindrical pipe (303) is characterized by having a predetermined length, which is calculated by a heat transfer model to ensure the cooling of the combustion emissions. This second section of cold zone cylindrical pipe (303) is joined by a joint of "clamp" type (2), to the third section of cold zone cylindrical pipe (304). The third cold zone cylindrical pipe (304) contains the injection nozzle of secondary air (306). Then, the third section of cold zone cylindrical pipe (304) is jointed to the fourth section of cold zone cylindrical pipe (305) through a joint type "clamp" (2), wherein the latter is connected to the zone for storing the combustion emissions (400) by a fastening clamping flange which lies within the flexible container (401).

The zone for storing the combustion emissions (400) is mainly formed by a flexible container (401), chemically inert, such as Tedlar® or Teflon®, and four or more connections for collecting samples (402). The zone for storing the combustion emissions (400) serves to collect the gases and particulate matter generated in the combustion chamber (200) by four or more connections for collecting samples (402) for the subsequent chemical and/or physical characterization of the emissions. The flexible container (401) fulfills the function as a storage lung of the emissions from where the samples are collected through the four or more connections for collecting samples (402), to which the various collecting samples devices are connected for further sample analysis.

Finally the controlled combustion system (1) is supported by three support braces (4) as it is shown in FIG. 1.

For the operation, considering that the controlled combustion system (1) is fully assembled at the beginning, it is necessary first to remove part of the pre-chamber, pulling the clamp joint (2) jointed to the first cold cylindrical pipe (101) with the second cold cylindrical pipe (101'). Once separated these pieces, the solid combustible is positioned in the ashtray (105). Then, carefully assuring that the solid combustible stays in place, the pre-chamber part (100) that was removed through the joint clamp (2), is rejoined. Then, the injection of combustive starts for a combustible-air ratio (RAC) determined through the injection pipe (104) and manually accommodating the ashtray (105) so that it is outside the cold cylindrical pipe (101) during switching on the electrical resistance of the adiabatic furnace (203) for preheating the combustion chamber (200). After preheating, and without turning off the electrical resistance (108) of the adiabatic furnace (203), the ashtray (105) is positioned with the solid combustible at the center of the combustion chamber (200) through four guides, visualizing through the front cover glass (103) that the positioning is correctly performed. Then, is operated immediately in the sequence and order mentioned, the electrical resistance (108) of the ashtray (105) to ignite the solid combustible, the gas analyzer, the injection of secondary air through the air injection nozzle (306), measuring the temperature at the thermocouple type K in the zone of the combustion chamber (200) where the ashtray (105) is located, and the four or more connections for collecting samples (402) of the Speciation Sampler® equipment are opened. Collecting samples is done until solid combustible burning ends completely.

Once the combustion is ended, the oxidizing supply is cut; the temperature of the adiabatic furnace is settled (203) at room temperature, preferably 20° C., and the collecting of samples stops when the container (401) pressure for storing samples is about 0.1 times of the atmospheric pressure.

When this pressure value is reached, the supply of oxidizing agent is changed by an inert gas supply, such as nitrogen, helium, among others, to a recommended flow of 10 [liter/min] with the purpose of purging the controlled combustion system (1) and helping to reduce the temperature of the combustion chamber (200).

During the purging process the four or more connections for collecting samples (402) of the Speciation Sampler® equipment must remain open.

It is advisable to perform collecting samples of waste gases and particles that the purge process could have removed, i.e. they can be sampled in the same way as is done with the combustion emissions, in order to verify the cleaning of the controlled combustion system (1) and to define the baseline for the next combustion experience. This procedure should be repeated until the baseline is obtained free of interferences according to chromatographic analysis.

Once the temperature of the adiabatic furnace (203) has adjusted to room temperature, the controlled combustion system (1) is disassembled. First, It is necessary to remove the gas analyzer, followed by the flexible container (401), then the heat transfer section (300) and finally the prechamber (100), in order to remove ashes and solid residues that may remain in the combustion chamber (200). The whole system is disassembled by removing the clamp connections (2).

In case the purge system with inert gas is insufficient, the system allows other types of cleaning, such as pyrolysis, chemical abrasion, mechanical abrasion, among others. The cleaning system is a voluntary choice for the user, according to the operational, analysis and collecting samples requirements.

In case that a violent pressure increase in the flexible container (401), is observed it is recommended to open the relief valve that the storage area of the combustion emissions (400) contains, assuming the associated sample loss as a measure to prevent an explosion of the flexible container (401).

The invention claimed is:

1. A controlled combustion system for the simultaneous analysis of the thermodynamic efficiency of combustion and pollutant emissions in solids with combustible potential, wherein it comprises:
a combustion prechamber, preferably cylindrical, which is formed with guides for the positioning of a solid combustible by an ashtray, a pipe for oxidizing gas injection inside said combustion prechamber, the ashtray connected to said pipe for oxidizing gas injection, an electric resistance located on said ashtray in direct contact with said solid combustible, one observation peephole and a first glass ring to isolate the high temperature of the combustion zone;
a sensor to measure the temperature in the combustion zone located on said ashtray;
a combustion chamber, preferably cylindrical, connected downstream of said first glass ring of the prechamber, which contains an adiabatic furnace for combustion of the solid combustible, for each batch of combustion;
a heat transfer unit, preferably cylindrical, connected downstream of the combustion chamber, comprising a second glass ring to isolate the high temperature of the combustion zone, and a connection for a combustion gas analyzer device to determine the performances of combustion and burning; and
a unit for storing the combustion emissions, connected downstream of the heat transfer unit with an attachment means and clamping that contains a container for storing samples made of a flexible, chemically inert material, and collecting samples means for the simultaneous collection of gases and particulate matter obtained from the combustion chamber, for the analysis of the combustion emissions.

2. The controlled combustion system of claim 1, wherein said system is made of a chemically inert material resistance to combustion temperatures.

3. The controlled system of claim 1, wherein the prechamber allows the injection of the oxidizing and positioning of the ashtray into the combustion chamber.

4. The controlled combustion system of claim 1, wherein the positioning of the solid combustible into the combustion chamber is accomplished by placing the solid combustible in the ashtray, which is accomplished by manually guiding the ashtray into said combustion chamber through four equidistant concentric guides which are fasten to a conical cap, which in turn seals the combustion chamber before the combustion process begins.

5. The controlled combustion system of claim 1, wherein the prechamber has a first cylindrical structure of cold zone, a second cylindrical structure of cold zone, a cylindrical structure of hot zone and a front cover glass connected to the prechamber for the visual analysis of the combustion zone.

6. The controlled combustion system of claim 1, wherein the adiabatic furnace is made of refractory ceramic and is equipped with an electrical resistance for generating the temperature to maintain adiabatically the combustion chamber throughout the combustion process, and which is surrounded by a heat insulator to prevent heat losses to the environment.

7. The controlled combustion system of claim 1, wherein the length of the cylindrical tube located in the heat transfer unit is calculated by a heat transfer model designed for the combustion chamber to achieve a suitable temperature of the combustion emissions and then be received and analyzed in the storage area of combustion emissions.

8. The controlled combustion system of claim 1, wherein a gas analyzer is installed in the initial part of the heat transfer unit, which can measure, among other chemicals, CO, $CO_2$, $NO_x$, $SO_x$, $O_2$ and temperature, and wherein the value of $CO_2$ allows determine the combustion efficiency and burning.

9. The controlled combustion system of claim 1, wherein in the heat transfer unit and prior to the unit for storing the combustion emissions is located an injection nozzle of secondary air, for cooling the combustion emissions and increasing the flow rate of emissions to the required value by the unit for storing the combustions emissions.

10. The controlled combustion system of claim 1, wherein the container for storing samples of the unit for storing the combustion emissions is made of a flexible, chemically inert material.

11. The controlled combustion system of claim 1, wherein the container for storing samples of the unit for storing the combustion emissions fulfills the function of a storage lung for gases and particulate matter, from where samples are collected by using four or more connections to the collecting samples means for subsequent sample analysis.

12. The controlled combustion system of claim 1, wherein the operational control of the controlled combustion system is performed through an automatic electronic control device which delivers several options with high reproducibility and repeatability between each experiment carried out under the same conditions.

13. The controlled combustion system of claim 1, wherein the controlled combustion system is supported by three support braces.

14. The controlled combustion system according to claim 1, wherein for the cleaning of the controlled combustion system the joints type "clamp" ensure easy assembly and disassembly of the controlled combustion system units.

15. A method for simultaneous analysis of the thermodynamic efficiency of combustion and pollutant emissions in solids with combustible potential in a controlled combustion system, wherein it comprises:
injecting an oxidizing gas to a controlled combustion system through oxidizing injection means through a prechamber, preferably cylindrical, which is formed with guides for the positioning of a solid combustible by an ashtray, one observation peephole, a pipe for oxidizing gas injection, an ashtray connected to said pipe for oxidizing gas injection, an electric resistance located on said ashtray, a sensor to measure the temperature in the combustion zone located on said ashtray, and a first glass ring to isolate the high temperature of the combustion zone;
defining a variable central volume that generates a flame in a combustion chamber, preferably cylindrical, connected downstream of said first glass ring of the prechamber to a quantity of solid combustible to be used for each batch of combustion;
recording the combustion temperature parameters in a heat transfer unit, preferable cylindrical, connected downstream of the combustion chamber, comprising a second glass ring to isolate the high temperature of the combustion zone, and a connection for a combustion gas analyzer device to determine the performances of combustion and burning;
collecting and storing gases and particulate matter simultaneously, obtained from the combustion, with a unit for storing the combustion emissions, connected downstream of the heat transfer unit;

analyzing the pollutant emissions of organic and inorganic compounds that allow to determine emission profiles and emission factors for each type of pollutant, molecular markers and concentration ratios of specific chemical compounds for kind of pollution sources, for the analyzed solids with combustible potential; and providing simultaneous results of thermodynamic efficiency and emissions analysis of the combustion solids.

16. The method for simultaneous analysis of claim 15, wherein the combustion chamber contains an adiabatic furnace for solid combustible combustion.

17. The method for simultaneous analysis of claim 15, wherein the gas analyzer can measure among other chemical compounds, CO, $CO_2$, $NO_x$, $SO_x$, $O_2$ and temperature, and wherein the value of $CO_2$ allows to determine the combustion and burning efficiency.

18. The method for simultaneous analysis of claim 15, further comprising measuring the temperature in the combustion zone with a sensor.

19. The method for simultaneous analysis of claim 15, wherein the positioning of the solid combustible into the combustion chamber is accomplished in the prechamber by manually guiding the ashtray into said combustion chamber through four equidistant concentric guides which are fasten to a conical cap, which in turn seals the combustion chamber before the combustion process begins.

20. The method for simultaneous analysis of claim 15, wherein the prechamber has a first cylindrical structure of cold zone, a second cylindrical structure of cold zone, a cylindrical structure of hot zone and a front cover glass connected to the prechamber for the visual analysis of the combustion zone.

21. The method for simultaneous analysis of claim 15, wherein in the heat transfer unit and prior to the unit for storing the combustion emissions an injection nozzle of secondary air is located, for cooling the combustion emissions and increasing the flow rate of emissions to the required value by the unit for storing the combustion emissions.

22. The method for simultaneous analysis of claim 15, wherein the unit for storing the combustion emissions has a container for storing samples which is made of an inert material that fulfills the function of a storage lung for emissions, from where samples are collected by using four or more connections to the collecting samples means for the subsequent sample analysis.

23. The method for simultaneous analysis of claim 15, wherein the operational control of the controlled combustion system is performed through an automatic electronic control device which delivers several options with high reproducibility and repeatability between each experiment carried out under the same conditions.

* * * * *